United States Patent [19]
Mazars

[11] Patent Number: 4,735,624
[45] Date of Patent: Apr. 5, 1988

[54] ALL-IN-ONE DIAPER WITH BRANCHED ABSORBENT PAD AND ITS METHOD OF MANUFACTURE

[75] Inventor: Paul Mazars, Louviers, France
[73] Assignee: Beghin-Say, S.A., Thumeries, France
[21] Appl. No.: 932,043
[22] Filed: Nov. 18, 1986
[30] Foreign Application Priority Data
Nov. 19, 1985 [FR] France .................. 85 17100
[51] Int. Cl.⁴ .............................. A61F 13/16
[52] U.S. Cl. .................. 604/378; 604/385.1
[58] Field of Search ............ 604/386.1, 368, 378
[56] References Cited
U.S. PATENT DOCUMENTS
4,413,995 11/1983 Korpman ................. 604/368
4,642,110 2/1987 Dudek .................. 604/385.1

Primary Examiner—John D. Yasko
Attorney, Agent, or Firm—A. W. Breiner

[57] ABSTRACT

The disposable all-in-one diaper of the type comprising an absorbent pad inserted between a sheet (1) impermeable to liquids and a permeable sheet (2), the diaper having in the longitudinal direction a crotch area (5) prolonged on both sides by a front trunk area (6) and a rear trunk area (7), said pad (3) being constituted by an absorbent material consisting essentially of hydrophilic fibres joined to one another in a manner such as to form a coherent structure covering a narrow part (31) corresponding to the crotch area (5), and widening out towards the front and rear areas, is characterized in that the pad consists, at least in the front trunk area, of at least three branches (32) placed longitudinally in the prolongation of the narrow part (31) diverging from one another so as to form cavities between sheets (1) and (2).

8 Claims, 1 Drawing Sheet

ALL-IN-ONE DIAPER WITH BRANCHED ABSORBENT PAD AND ITS METHOD OF MANUFACTURE

The invention covers a disposable all-in-one diaper of the type intended to absorb and retain body liquids of babies and incontinent adults. It relates in particular to the form of pad incorporated in the diaper.

All-in-one diapers as known comprise an absorbent pad consisting essentially of cellulose fibres obtained by dry grinding paper pulp sheets, covered on a first face by a sheet impermeable to liquids made of a flexible, strong thermoplastic material such as polyethylene. This sheet forms the outer face of the diaper; it fulfils at the same time a support function and prevents the escape of liquids that could pass through the absorbent pad.

The opposite face of the absorbent pad is covered by a sheet, generally non-woven, permeable to liquids. This sheet, defining the inner face of the diaper maintains the pad fibres in position and comes into contact with the skin of the user. It is of a nature which allows body liquids to pass through it easily in order to allow their rapid absorption by the underlying pad.

The two sheets, permeable and impermeable, are joined to one another, edge to edge, in a manner such as to enclose completely the absorbent pad. The diaper is of a generally rectangular form, it can be folded over onto itself longitudinally in the crutch area so that its transversal dimension is small in this location. This objective is also attained by rounded cut-outs representing the contour of the upper parts of the thigh.

The width of the diaper in the front trunk area and the rear area corresponds substantially to the width of the pelvis of the user for whom the diaper is intended, so that the diaper, after fitting, envelops the pelvis as hermetically as possible to prevent any lateral leaks.

In order to avoid leaks the absorbent pad must be made to cover the greatest possible area for at least two reasons: the first relates to the absorptive capacity of the pad, which depends on the volume occupied by the fibres. The second reason is that the pad must be able to collect, over an extensive area, the liquids migrating along the diaper. This applies in particular to male users.

Furthermore this type of fibre pad has the disadvantage, besides being bulky, of having a low liquid diffusion capability. Absorption remains localized in the penetration area so that its total absorption capacity is not used optimally.

A proposal to overcome this has already been made by providing in the pad some lines, densified by compaction, oriented in defined directions. U.S. Pat. No. 2,788,003 describes an example of its embodiment. For by compressing the pad locally, the space between the fibres is reduced, which facilitates conduction by capillarity. It is thus possible to improve the distribution of moisture through the pad. However, this method does not reduce the volume of the pad.

In order to limit the thickness it requires to fulfil its function it has been suggested that the cellulose fibres be joined to one another by incorporating thermo-meltable fibres which are incorporated in the mass when the pad is being made and melting these so as to make the cellulose fibres adhere to one another by means of this binder.

The invention provides a pad which ensures both a good distribution of the liquids, a greatest possible collection area, at least in the front trunk area likely to collect the liquids, while being very economic to produce.

According to the invention a disposable all-in-one diaper comprising an absorbent pad inserted between a sheet permeable and a sheet impermeable to liquids, the diaper having in its longitudinal direction a crotch area prolonged on both sides by a front trunk area and a back trunk area, said pad being constituted by an absorbent material consisting essentially of hydrophilic fibres joined to one another in a manner such as to form a coherent mass covering a narrow part corresponding to the crutch area widening out towards the front and back trunk areas said diaper being characterized in that the pad consists, at least in one of the trunk areas, of at least three branches placed longitudinally in the prolongation of said narrow part diverging from one another so as to provide cavities between them and the inner and outer sheets.

The pad preferentially comprises more than three branches extending from the central crotch area. Their number must depend on the application and size of the diaper. Their number is preferably odd so that one of the branches lies in the longitudinal axis of the diaper. In addition, this branch can be wider than the others. The space left between two adjacent branches must not be too large and the width of the branches must not be too small having regard to the solidity of the pad.

In order to improve absorption capacity, it is possible to incorporate particles known under the name of superabsorbents in the mass. These are compounds insoluble in water but which swell in the presence of a liquid which they can absorb in a quantity corresponding to several tens of times their dry weight. Their obvious importance has led manufacturers of disposable hygienic artices to mix them with cellulose fibres. But they nevertheless have the disadvantage of forming a barrier after a first swelling, so that the liquid slides on the already wetted part without being able to penetrate the deeper layers of the pad. By dividing the pad as provided for by the invention, the effective surface in immediate contact with the liquid is increased. The liquid is absorbed through the surface in contact with the skin of the user and also through the portions of the surface placed transversally. The absorption rate is thereby increased and the absorptive capacity of the pad after a first wetting improved.

The layout of the pad in longitudinal branches or ramifications spread out in fan form also provides a maximum surface for collecting liquids for a minimum quantity of material used and enabling production costs to be minimized. For in regard to a diaper of the prior art one starts with a fibres pad of width equal to that of the trunk areas which are cut out laterally to form a crutch area. To make a diaper according to the invention one starts on the contrary with a pad of width equal to the crutch area whose ramifications are arranged in the form of fan to make trunk areas. Thus not only is no waste produced but less material is used to cover a same surface.

Furthermore, the branches constitute so many barriers for run-offs or seepages moving in the transversal direction with respect to the diaper, thereby limiting the risks of leaks through the sides. Thus the problem encountered with the prior art pad is due not so much to the total absorptive capacity of the pad as the absorption of liquids before they have migrated towards the edges of the diaper and soiled the garments of the user. By this arrangement, the transversal migrations are slowed down and longitudinal migrations promoted to move in the direction of the cavities which form drains to the central crotch area of the pad.

Finally by reducing the volume of the absorbent mass in the front trunk part, compared with known articles, the diaper gains in flexibility. User comfort is improved and wear under garments more discreet.

Other characteristics and advantages will become apparent by reading the following specification of a mode of a non-limitative embodiment of the invention in which:

FIG. 1 shows an all-in-one diaper disposable after use according to the invention, as seen from side of the inner, non-woven face of which a detail is depicted to show the inner absorbent pad.

Figure 1:
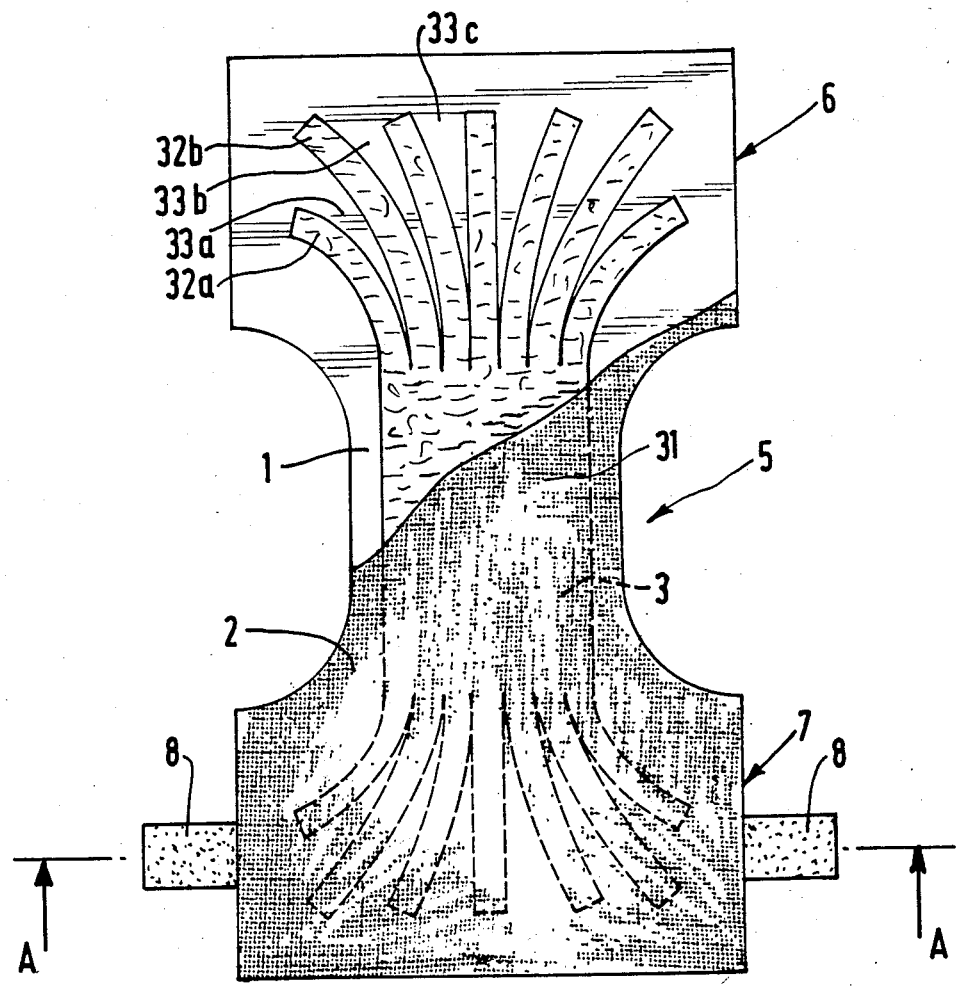
FIG. 1 shows an all-in-one diaper disposable after use.
Figure 2:
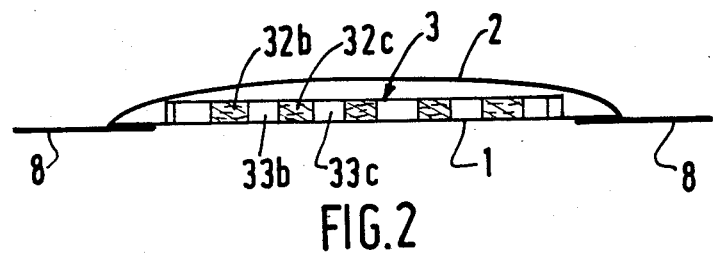
FIG. 2 shows a sectional view 1 along AA.

The diaper therefore comprises a support sheet 1 of strong, flexible material, impermeable to liquids and constituting the outer face of the diaper when it is being worn. The material that is generally used is polyethylene, but other plastic material would be equally suitable.

A sheet 2 of material permeable to fluids is placed on the support sheet, this sheet constitutes the inner face of the diaper and comes into contact with the skin of the user; it is made of non-irritant material through which body liquids pass easily, preferentially the material should be hydrophobic in order to maintain the sheet in a dry surface state. It can be a non-woven textile made from fibres obtained by the extrusion o thermoplastic materials, for example, non-woven material sold under the trade name of HOLNEST by the applicant. Other materials have the same properties known to the man of the art. The two sheets are welded or joined by gluing to one another at least edge to edge so as to form a closed envelope. Inside this envelope is enclosed the absorbent pad according to the invention, designed to collect and contain the body liquids having passed through sheet 2.

As is known the pad consists of hydrophilic fibres, in particular fibres obtained by dry grinding paper pulp. For the needs of the invention the pad has been made coherent, for example, by mixing, during the formation of the layer, with thermomelting fibres in quantities sufficient to allow the cellulose fibres, after melting and cooling, to adhere to one another without losing their absorptive capacity. An example of the embodiment of such a structure is described in Fr Pat. No. 2,256,279.

Inside the pad superabsorbent particles have also been mixed with the fibres. The best known products are alginates, cross-linked carboxymethyl celluloses, grafted starches, synthetic derivatives of the acrylamide type or the acrylate type.

The diaper has a narrow central crutch area 5, a front trunk area 6 and rear trunk area 7. On the support sheet of the latter are secured by attaching means 8 consisting in the manner known of fastners made of paper or other material bonded to one face.

The pad 3 placed on the support sheet comprises a narrow, central area 31, widening out towards the front and rear areas. According to the invention, the part of the pad relating to the front trunk area and possibly the rear trunk area is shaped into branches or ramifications diverging from one another 32a, 32b, 32c, etc. and forming between them and the cover sheets 1 and 2, cavities 33a, 33b, etc. These cavities have a form which tapers towards the central area. The number of branches 32 to be provided is at least three, but will depend basically on the application and the size of the diaper. It can be chosen from between 3 and 19, preferably 3 and 11, if odd, one of the branches must be placed in the longitudinal axis of the diaper. It can then be wider that the others.

A simple means of making a pad having the characteristics according to the invention, consists in preparing an absorbent pad in the form of a strip of the same width as that of the crotch area 31, in practice between 8 and 25 cm, and of length corresponding to the length specified for the pad, 70 cm for example. As the pad is coherent, it is possible to make, in the longitudinal direction, some notches of length determined from one end of the tape or both ends if it is desired to embody the invention for two trunk areas; branches 32 attached to a non-cut out part 31 are thereby obtained. The length of the branches corresponds substantially to that of the trunk areas. Their width depends on their number, for example, for a 15 cm-wide pad 5 branches, each of 3 cm, or 10 branches of 1.5 cm can be cut out.

The pad prepared in this way is placed on a support sheet. The strips are spread out fan-wise so as to cover the desired surface. To revert to the preceding example, a fan is formed whose largest width is less than 50 cm, preferably 40 cm. Spacing 33 can be same between all the ramifications, it can be non-uniform, for example, it is possible to bring the central ramifications closer together. The ratio of the largest width to the smallest width of the fan made thereby must, however, be less than five, preferably between 2 and 4. After the pad has been positioned, it is maintained on a sheet by means of an adhesive or welding. There are no particular points as regards the rest of manufacture of the diaper.

In use, the liquids pass through the permeable sheet 2, are absorbed partly directly by the branches of the front trunk area by penetrating it by the face placed on the skin side of the user and the lateral faces. Cavities 33 ensure rapid flow along these branches, bringing the liquids in contact with the pad over a large surface for rapid and extensive absorption, if necessary, the liquids reach the central area for total absorption.

Due to the longitudinal layout, each of the branches forms a barrier to the migration of the liquids in the transversal direction, the corresponding cavity always bringing them back to the longitudinal direction.

The invention is not limited to the embodiment described, it englobes in particular all the equivalents within reach of the man of the art.

What is claimed is:

1. A disposable all-in-one diaper comprising an absorbent pad inserted between a sheet impermeable to liquids and a sheet permeable to liquids, said diaper having in the longitudinal direction a crotch area, and a front trunk area and a rear trunk area extending from said crotch area; said front and rear trunk areas being of a width greater than said crotch area; said absorbent pad comprising an absorbent material containing hydrophilic fibers joined to one another in a manner so as to form a coherent structure substantially coextensive in width to said crotch area and containing a plurality of slits in said trunk areas to form a plurality of branches of pad material extending from said crotch area, said branches being fanned out to diverge from said crotch area toward the end of said trunk areas to form spaces which become progressively wider between said branches toward the end of said trunk areas remote from said crotch area.

2. The diaper according to claim 1 wherein said branches are of an odd number.

3. The diaper according to claim 2 wherein one of said branches is placed in the longitudinal axis of the pad with its width being greater that that of adjacent branches.

4. The diaper according to claim 1 wherein particles of superabsorbent product are incorporated in the absorbent mass.

5. A method of making a diaper comprising the following steps:
preparing a substantially rectangular absorbent pad comprising a crotch area and front and rear trunk areas extending from said crotch area;
forming a plurality of slits in the longitudinal direction of said pad extending from the crotch area to the ends of said front and rear trunk areas to form a plurality of branches;
positioning of said absorbent pad on a support area which is one of a liquid-impermeable sheet or a liquid-permeable sheet;
fanning out said branches to diverge from said crotch area toward the end of said trunk areas to form spaces which become progressively wider between said branches toward the end of said trunk areas remote from said crotch area whereby the largest width to smallest width ratio is between 1 and 5, and
applying the other of a liquid-impermeable or liquid-permeable sheet to the unsupported surface of said pad.

6. The method according to claim 5 wherein said ratio is between 2 and 4.

7. The method according to claim 5 wherein the width of said rectangular pad is between 8 and 25 cm.

8. The method according to claim 5 wherein the width of the fanned area is less than 50 cm.

* * * * *